US010579203B2

(12) United States Patent
Zamir et al.

(10) Patent No.: US 10,579,203 B2
(45) Date of Patent: Mar. 3, 2020

(54) WELLNESS MIRROR

(71) Applicant: Intel Corporation, Santa Clara, CA (US)

(72) Inventors: Nadav Zamir, Raanana (IL); Itai Druker, Rosh Ha'ayin (IL); Chia-Hsun Jackie Lee, Palo Alto, CA (US); Camila Dorin, Tel Aviv (IL); Barak Hurwitz, Kibbutz Alonim (IL); Amit Shahar, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 519 days.

(21) Appl. No.: 15/280,466

(22) Filed: Sep. 29, 2016

(65) Prior Publication Data
US 2017/0296874 A1 Oct. 19, 2017

Related U.S. Application Data

(60) Provisional application No. 62/322,186, filed on Apr. 13, 2016.

(51) Int. Cl.
| | |
|---|---|
| *A61B 5/00* | (2006.01) |
| *A61B 5/11* | (2006.01) |
| *G06F 3/0481* | (2013.01) |
| *G09B 19/00* | (2006.01) |
| *A61B 5/107* | (2006.01) |
| *A61B 5/024* | (2006.01) |
| *G06T 11/20* | (2006.01) |
| *G16H 40/63* | (2018.01) |
| *A61B 5/08* | (2006.01) |
| *A61B 5/0205* | (2006.01) |

(Continued)

(52) U.S. Cl.
CPC .......... *G06F 3/0481* (2013.01); *A61B 5/0046* (2013.01); *A61B 5/0079* (2013.01); *A61B 5/0205* (2013.01); *A61B 5/02427* (2013.01); *A61B 5/0816* (2013.01); *A61B 5/1079* (2013.01); *A61B 5/1128* (2013.01); *A61B 5/165* (2013.01); *A61B 5/4869* (2013.01); *A61B 5/7271* (2013.01); *G06F 19/00* (2013.01); *G06T 11/206* (2013.01); *G09B 19/00* (2013.01); *G09B 19/0092* (2013.01); *G16H 40/63* (2018.01); *G06T 2200/24* (2013.01)

(58) Field of Classification Search
CPC ............ H04N 5/243; A61B 5/00; G06K 9/80
See application file for complete search history.

(56) References Cited

U.S. PATENT DOCUMENTS

| | | | |
|---|---|---|---|
| 8,062,220 B2 * | 11/2011 | Kurtz | A61B 5/0059 348/222.1 |
| 2010/0277571 A1 * | 11/2010 | Xu | G06T 17/00 348/47 |

(Continued)

*Primary Examiner* — Phi Hoang
(74) *Attorney, Agent, or Firm* — Schwegman Lundberg & Woessner, P.A.

(57) ABSTRACT

Various systems and methods for providing a wellness mirror are provided herein. A system for providing a wellness mirror includes a display; a modeler to receive depth images from a depth camera that is communicatively coupled to the system, and provide a model of a subject in the depth images; a health profiler to analyze the model and produce a health and wellness analysis; and a user interface to present the health and wellness analysis on the display.

21 Claims, 10 Drawing Sheets

(51) Int. Cl.
*A61B 5/16* (2006.01)
*G06F 19/00* (2018.01)

(56) References Cited

U.S. PATENT DOCUMENTS

| | | | |
|---|---|---|---|
| 2014/0088995 A1* | 3/2014 | Damani | G06F 19/3418 |
| | | | 705/2 |
| 2015/0105670 A1* | 4/2015 | Bresch | A61B 5/0077 |
| | | | 600/479 |
| 2015/0154322 A1* | 6/2015 | Fonte | G02C 13/001 |
| | | | 351/178 |
| 2015/0154453 A1* | 6/2015 | Wilf | G06K 9/00711 |
| | | | 382/103 |
| 2015/0306496 A1* | 10/2015 | Haseltine | H04L 65/403 |
| | | | 463/31 |
| 2015/0320622 A1* | 11/2015 | Seitz | A61F 13/55115 |
| | | | 604/385.02 |
| 2015/0329048 A1* | 11/2015 | Wang | G06T 7/80 |
| | | | 348/148 |
| 2016/0001131 A1* | 1/2016 | Radecka | G01C 22/006 |
| | | | 702/160 |
| 2016/0206485 A1* | 7/2016 | Seitz | A61F 13/55105 |
| 2017/0055878 A1* | 3/2017 | Chon | A61B 5/0816 |
| 2017/0200218 A1* | 7/2017 | Napper | G06Q 10/08 |

* cited by examiner

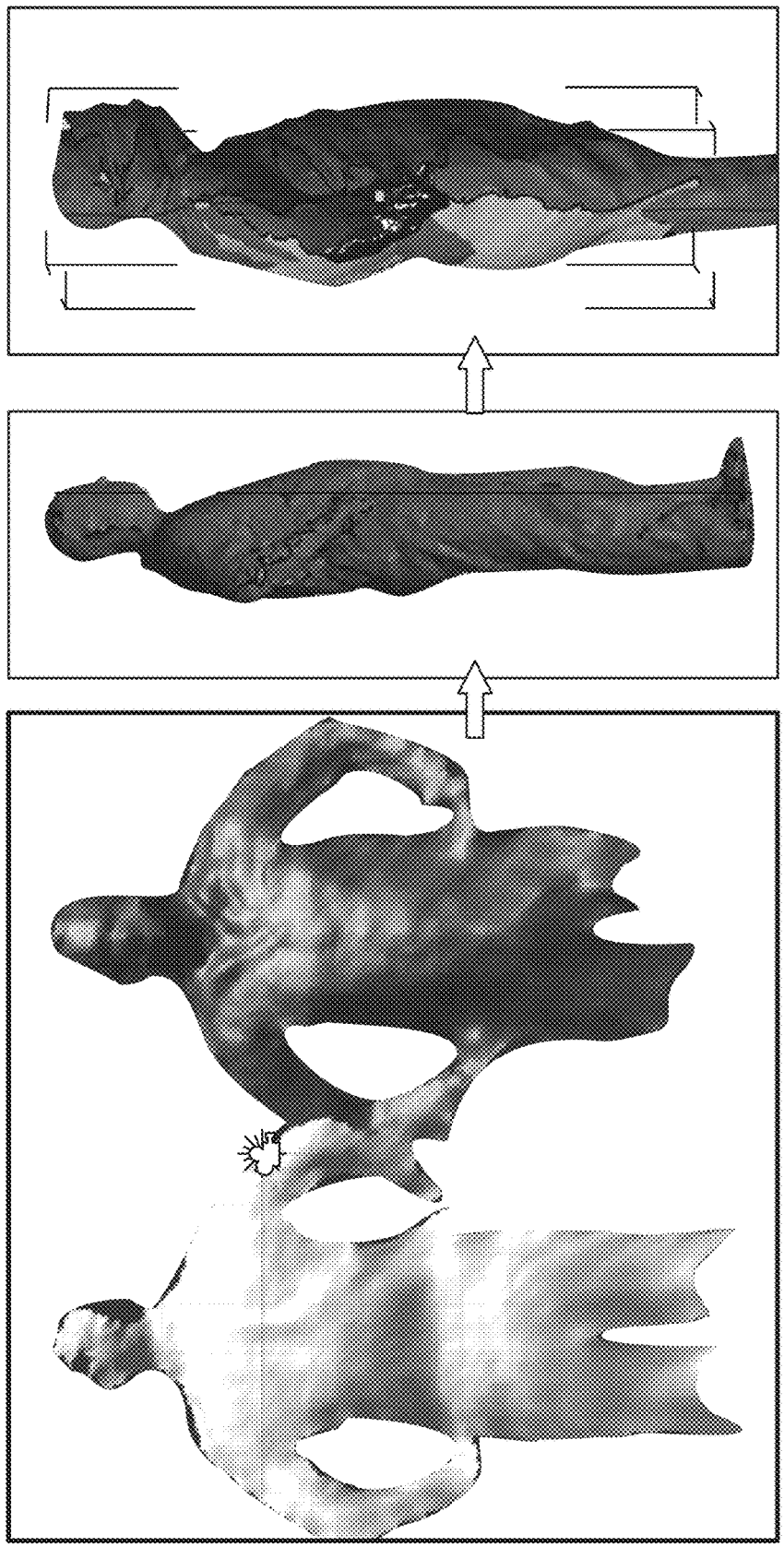

WELLNESS MIRROR

CLAIM OF PRIORITY

This patent application claims the benefit of priority U.S. Provisional Patent Application Ser. No. 62/322,186, titled "Wellness Mirror," filed on Apr. 13, 2016, which is hereby incorporated by reference herein in its entirety.

TECHNICAL FIELD

Embodiments described herein generally relate to health monitoring apparatus and in particular, to a wellness mirror.

BACKGROUND

Smart devices, such as smartphones, smart watches, and even exercise equipment are used in everyday activities to improve one's health and wellbeing. Some smart devices are used to monitor various aspects of a person's health and wellness on a period or continual basis. Tracking a person's state over time provides for earlier diagnosis, helpful feedback, or other useful information.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which:

FIG. 3A is a schematic diagram illustrating data and control flow, according to an embodiment;

DETAILED DESCRIPTION

In the following description, for purposes of explanation, numerous specific details are set forth in order to provide a thorough understanding of some example embodiments. It will be evident, however, to one skilled in the art that the present disclosure may be practiced without these specific details.

Smart devices have emerged in our lives for the past couple of years, from the smartphone in one's pocket to the smart refrigerator in one's kitchen. The present systems and methods provide a smart mirror with an integrated 3D camera that enables advanced health and wellness analysis of a user in real-time, including body measurement and sports tracking.

By integrating a 3D camera in a mirror form factor, the present system provides more intuitive interaction, 3D body measuring, object tracking, and height measurement. Other aspects will become apparent to one of ordinary skill in view of the present disclosure.

Several problems exist when using a 3D camera, including measuring a person using a static camera located in a fixed location on the mirror facing the user, identifying the user's height, pulse, breathing and maximal oxygen consumption (VO2 max) and providing useful information based on these measures. The present disclosure provides various mechanisms to address these issues. The system is further able to provide a seamless experience to the user, tracking data over time and providing high order analysis by combining these results.

In general, a 3D wellness mirror, as disclosed herein, is a smart mirror that may detect various biometrics of a user, and track them over time. Integrated into the overall design is a 3D depth camera that uses depth sensing technology to take measurements of the user without having the user to fully undress. The system is further able to measure various high order biometric information of the user (e.g., pulse, breathing rate, basal metabolic rate (BMR), body mass index (BMI), etc.), without having the user needing to wear any dedicated devices.

By calculating different biometrics and tracking them over time, the system has a higher level of understanding and is more capable of detecting anomalies with higher confidence. In an embodiment, the system is produced in a mirror form factor, which is a device that users normally stand in front of on a daily basis. As such, the user's daily routine is not impacted and user measurements and tracking are seamless (e.g., the user is not required to add another task of health measurement to his daily routine).

Figure 1:
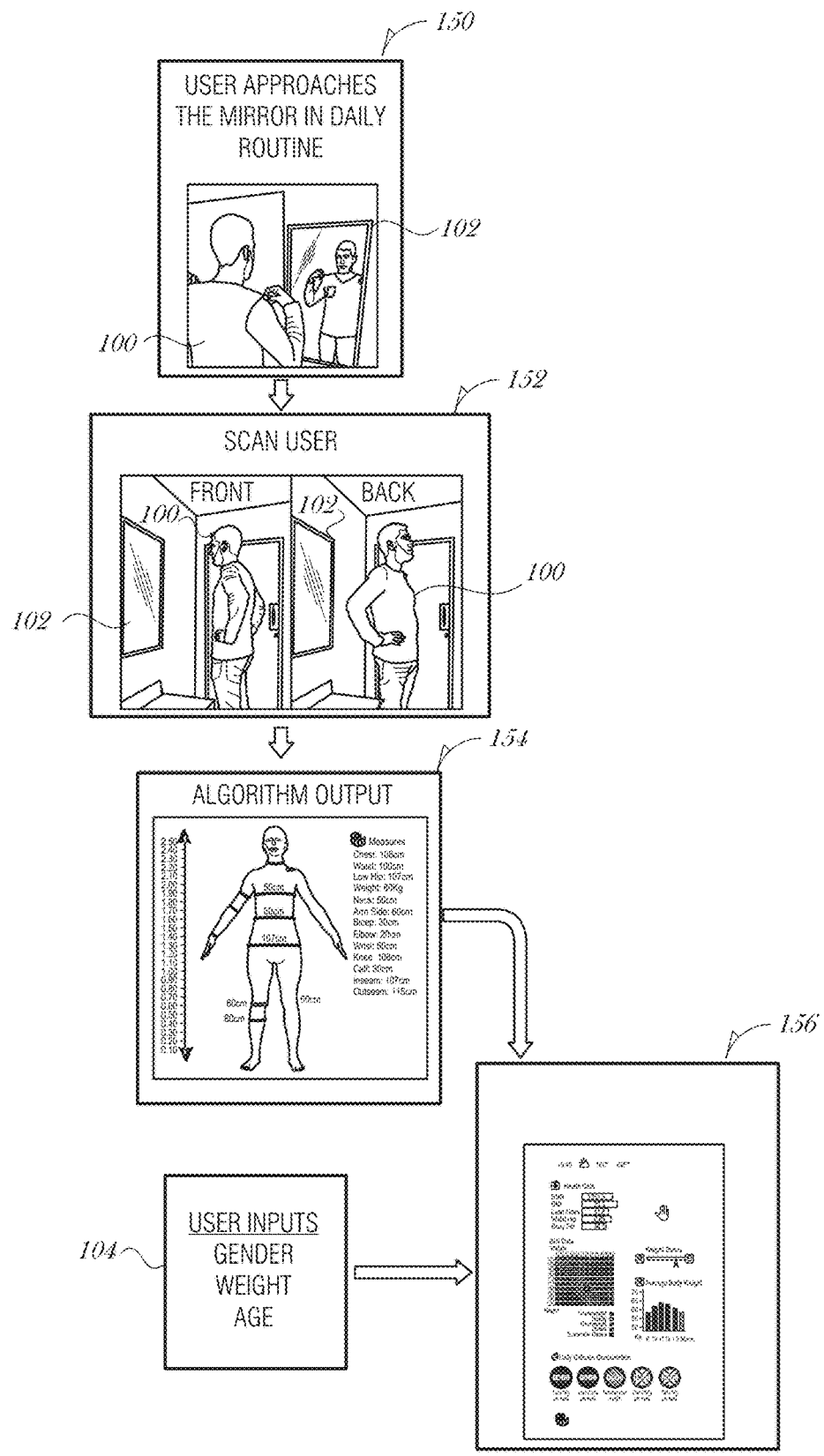
FIG. 1 is a schematic diagram illustrating data and control flow, according to an embodiment.

FIG. 1 is a schematic diagram illustrating data and control flow, according to an embodiment. The user 100 approaches the wellness mirror 102 in his daily routine (event 150). The user 100 may be prompted to pose facing toward and away from the mirror 102, or the user 100 may be captured as the user 100 is moving about the mirror 102 (event 152). Based on images collected while the user 100 is moving about the mirror 102, various biometric parameters are determined and output (event 154). The biometric parameters are used in combination with user inputs 104, to produce high order health information, which may be presented to the user 100 (event 156). The user 100 may have the health information presented on the wellness mirror 102 or on an auxiliary device (e.g., a smartphone, a laptop, a tablet, or other user device).

The mirror 102 may include or be coupled to a weight sensor placed on the floor. The weight sensor may provide a convenient target for the user to stand on while having their images captured by the 3D depth camera. The weight sensor may be incorporated into a mat with icons, drawings, or other insignia to instruct and guide the user to the proper position to stand while being scanned. The weight sensor, which may be an electronic scale, may be coupled directly or wirelessly to the mirror 102. For instance, the weight sensor may be coupled using Bluetooth or Wi-Fi, in various embodiments. Alternatively, the weight sensor may be wired into a port on the mirror 102, such as a Universal Serial Bus (USB) port.

After collecting user information, various outputs may be provided to the user 100, such as presenting to the user 100 an amount of calories that should be consumed today to gain 1 kg weight or a running distance to lose 0.5 kg. Furthermore, by gathering and tracking the user's biometrics over time, the system is able to show changes during different periods (e.g., summer vacations may result in decreased physical activity) and may offer the user 100 different activities.

In an example, the user 100 may provide their weight, gender, and age to the mirror 102. The user 100 may provide such input using various input modalities, for example voice input, touch input (e.g., on a virtual keyboard presented on the mirror 102), gesture input (e.g., selecting numbers or letters from a virtual keyboard interface presented on the mirror 102), with an auxiliary device (e.g., inputting information from a smartphone that is paired to the mirror 102), or other mechanisms. Using the 3D depth camera, the mirror 102 may estimate the user's height. With the height, weight, gender, and age, the mirror 102 may use a Harris-Benedict equation to estimate a BMR of the user.

As another example, to estimate the body mass index (BMI) of a user, the mirror 102 may receive the weight of the user 100 from various input modes. For example, the user 100 may input their weight using one of the modes described above with respect to the BMR embodiment. As another example, the user 100 may stand on an electronic scale that is coupled to the mirror 102, as described above. Using the 3D depth camera, the mirror 102 may estimate the user's height. With the weight of the user 100 and the estimated height, the BMI may be determined by comparing a ratio of the user's weight and height. One example BMI calculation is to divide the weight by the squared height and multiply the result by 703, with consistent units of measurement (e.g., kilogram/meter$^2$*703 or lb/in$^2$*703). BMI provides a rough calculation of a user's body composition and ranges have been established to provide insight into whether a person is underweight, normal, overweight, or obese. Other BMI calculations may be used without departing from the scope of this disclosure. Examples of alternative BMI measurements take into consideration waist circumference (e.g., estimated using image analysis on the 3D image), waist-to-hip ratio, body surface area, The 3D depth camera may also be used to provide intuitive control and interaction with the wellness mirror 102, such as by supporting different hand gestures, voice interaction, and face recognition capabilities. As an example, as the user 100 approaches the wellness mirror 102 (event 150), the user 100 may wave his hand causing the mirror 102 to activate. The wave may be a predetermined gesture and may be configured by the user 100 to train the mirror 102. A user interface may be overlaid or projected onto the mirror 102, for example from behind the mirror 102. The user 100 may navigate the user interface, provide user input and selections, or otherwise control the mirror 102 via the user interface with gestures, voice commands, touching the mirror 102 with gestures, or combinations of such modalities. The mirror 102 may prompt the user 100 to perform actions, such as to stand in a certain pose or place their front or back toward the mirror 102 for scanning. The prompts may be voice prompts or on-screen user interface prompts. The 3D depth camera may be used to determine whether and when the user 100 complies, for instance, by recognizing that the user's face or rear are recognized as being pointed toward the mirror 102.

Figure 2A:
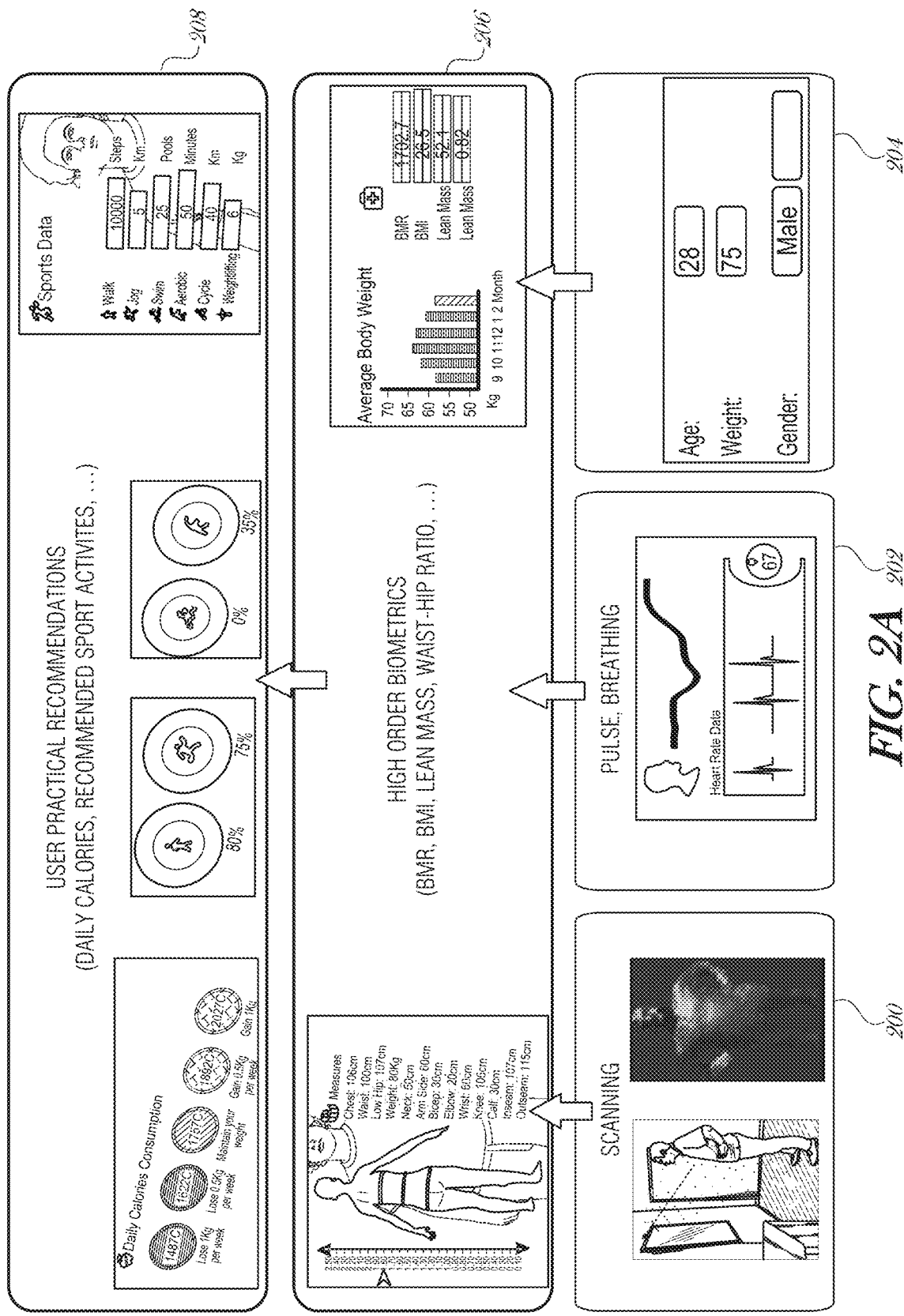
FIG. 2A is a schematic diagram illustrating data and control flow, according to an embodiment.
Figure 2B:
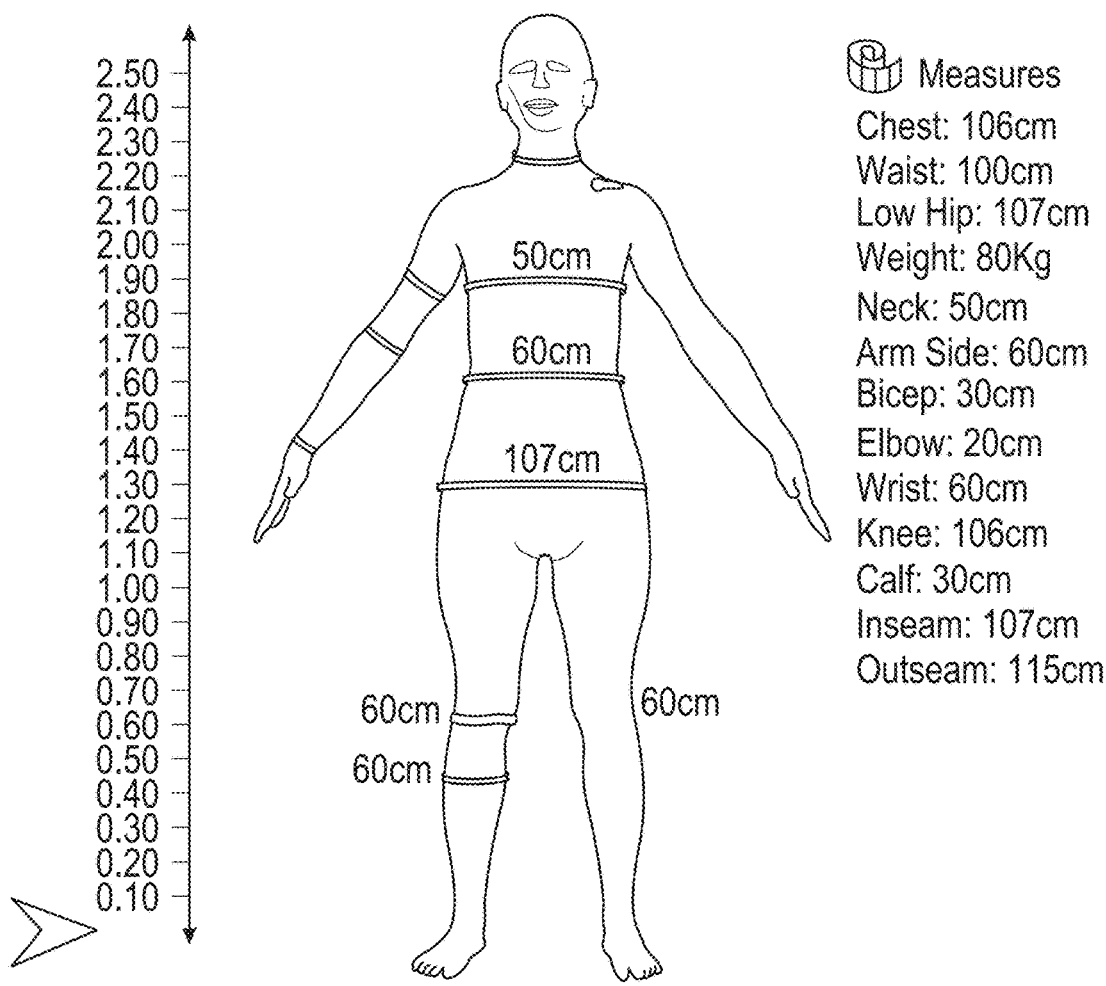
FIG. 2B illustrates a user interface of high order biometrics, according to an embodiment.

FIG. 2A is a schematic diagram illustrating data and control flow, according to an embodiment. Information from body scans (data 200), measured biometrics (data 202) such as pulse or breathing rate, and user inputs (data 204) may be fused and analyzed to determine high order biometrics (data 206), such as BMR, BMI, lean mass, waist-hip ratio, etc. FIG. 2B illustrates a user interface of high order biometrics, according to an embodiment. This high order biometric data (data 206) may then be used in various functions, calculations, or analyses to provide practical recommendations and other output (data 208) to the user. The practical recommendations and other output (data 208) may be information like daily caloric consumption, suggested modes of travel or exercise, amount, or frequency of exercise, historical data, or the like.

The pulse, breathing rate, or other measured biometrics (data 202) may be measured by the body scanning (data 200). Pulse may be determined optically using a mechanism, such as that described in FIG. 5. Breathing rate may be measured by taking a video or several images over time, and measuring the increase and decrease of the chest region of the person. The increasing/decreasing of the chest region may be time correlated, resulting in an estimated breathing rate. Shoulder movement, head movement, and other motion may be used as well to determine an estimated breathing rate.

Figure 3B:
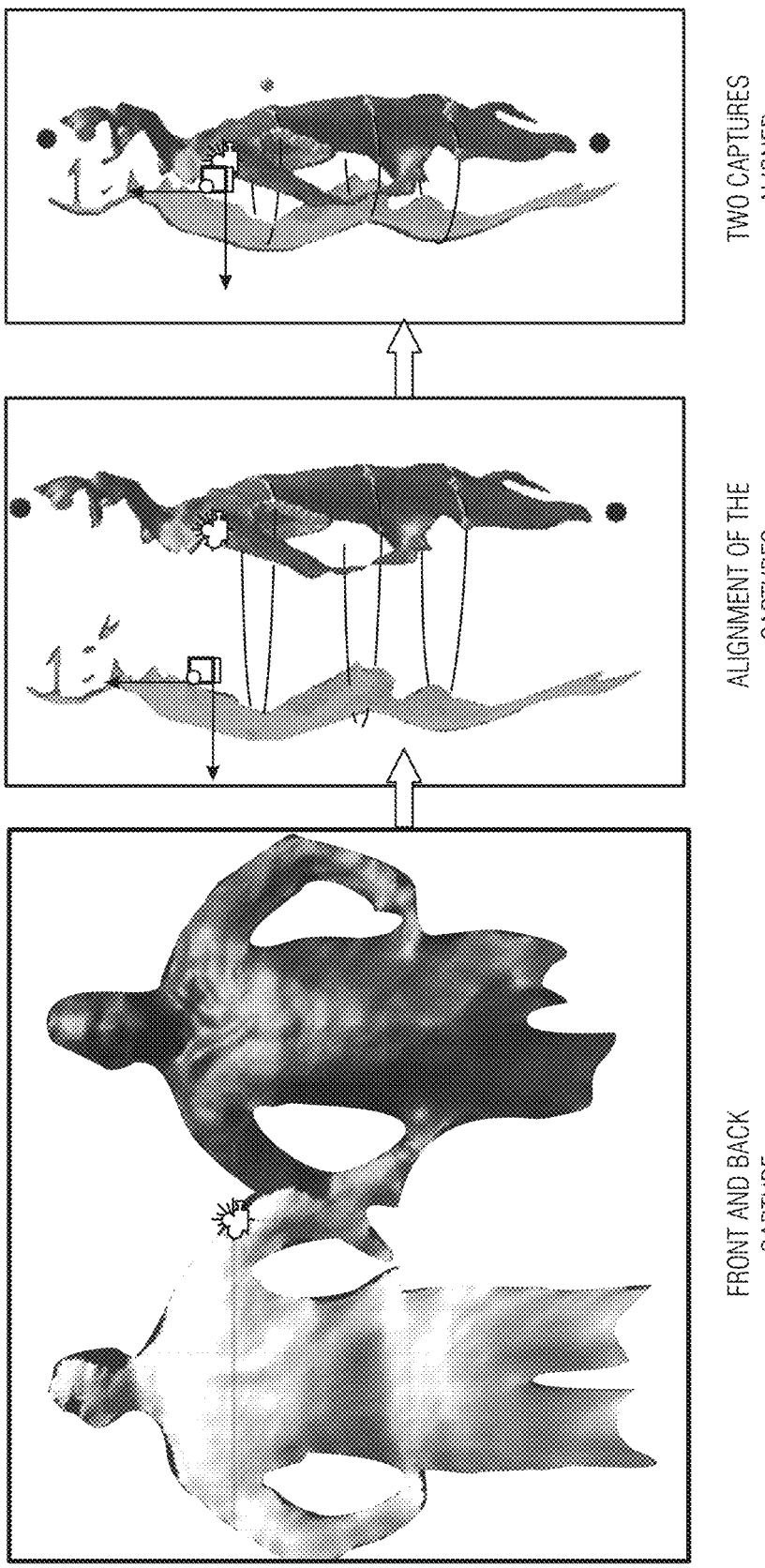
FIG. 3B is a schematic diagram illustrating data and control flow, according to an embodiment.

FIGS. 3A-3B are a schematic diagrams illustrating data and control flow, according to embodiments. Conventional systems require a full body scan from a continuous scan as the user rotates or from many different angles, in order to acquire enough data to compose a model of the user. In contrast, the present systems and methods use a front and back capture of the user, and then compose these two captures into a total model.

In another aspect, previous systems required gathering a complete scan of the user, creating his virtual avatar and measuring over it, a process which took several minutes, requiring assistance by a second person holding a tablet and scanning around the user. The present system instead uses a novel intuitive process of gathering the user's measurements and biometrics by taking merely two captures of the user—front and back captures, and using loose cloth body measurement techniques to build the user model. Using two scans instead of a continuous scan may result in a less expensive market price, a simplified user experience, and a more durable product.

As is illustrated in FIG. 3A, partial information is obtained by a front and back capture (stage 300). The two captures are aligned to produce a full capture (stage 302), where the front and back captures have been aligned (stage 304). Capture alignment, rotational corrections in the x and y axes, and height measurement are provided by using a camera that looks at the user from above (e.g., downward facing toward the user). FIG. 3B is another illustration of how partial body information (front and back captures) are aligned to form a model of the user.

Upon installation of the wellness mirror, the user may perform an initial calibration assisted by another person. Initial calibration may include calibrating the camera (e.g., measuring and inputting the camera's height off of the floor), orienting the camera, framing the subject with pan/zoom controls, or the like. Once calibrated, the user may input his personal details (e.g., age, gender, ethnicity, etc.), which is stored in his personal profile for future use. Later, when the user approaches the wellness mirror he is recognized by the integrated camera and the mirror activates, enabling interactions using voice and hand gestures. When initiated, two captures of the user are taken (front and back) along with automatic pulse and breathing measurements, after which his measures, height and high order biometrics are automatically calculated, stored and compared with past scans. Based on these results different recommendations may be displayed to the user, such as recommended calories and sports activities.

The user's planned activities may be accessed by connecting to his calendar or any wearable devices including, but not limited to smart watches, digital weights, exercise apparatus, and smart bracelets. The planned activities may then be incorporated into the suggested sports activities, exercise, etc.

Being able to measure body metrics by taking merely two captures and without compelling users to fully undress creates a seamless health tracking experience as part of the user's daily routine. Additionally, by leveraging the short range interaction capabilities of 3D depth cameras, the system enables intuitive interaction with the device using other input modalities, such as face recognition and hand gestures. Moreover, by gathering the user information and analyzing it with respect to current scans, the system is able to provide accurate high order biometrics and health analysis for the users.

Figure 4:
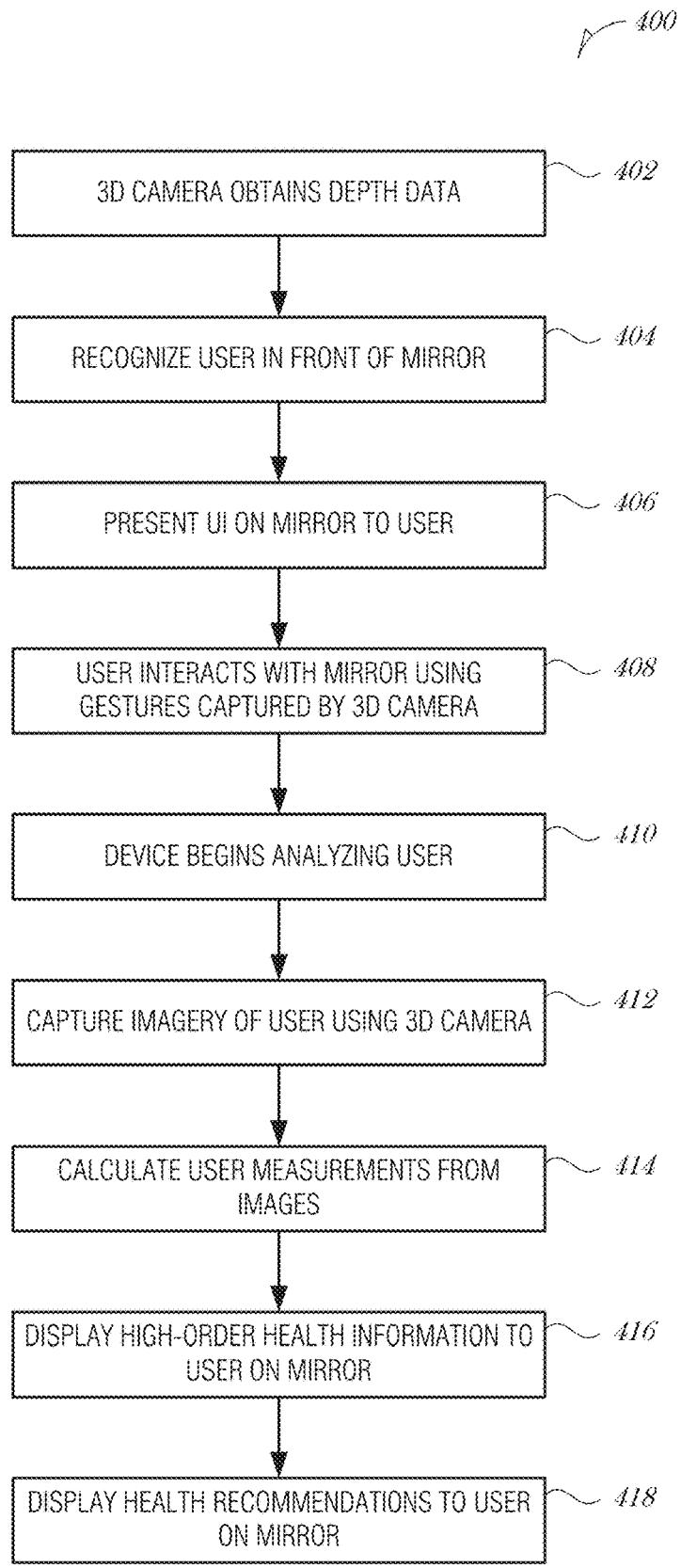
FIG. 4 is a flowchart illustrating control and data flow, according to an embodiment.

FIG. 4 is a flowchart illustrating control and data flow 400, according to an embodiment. Real-time get depth data from world facing 3D camera is obtained (operation 402). As the user stands in front of the mirror, his face is detected and recognized in real-time (operation 404). A customized menu appears to the user. The menu may be accompanied with past health results in the user interface (operation 406). The user interacts with the mirror using hand gestures, facial gestures, etc. (operation 408) as user decides to do health and wellness analysis, and the device enters the health analysis mode (operation 410). Real-time depth sensing is carried out to capture the user's body (operation 412). 3D data is analyzed and user's measurements, height, and biometrics (e.g., pulse, breathing) are calculated (operation 414). High-order health information is displayed to the user (e.g. BMI, body fat and waist-hip ratio) (operation 416). Practical recommendations may then be displayed based on the current and past measures (e.g., recommended calories per day, sports activities) (operation 418).

Figure 5:
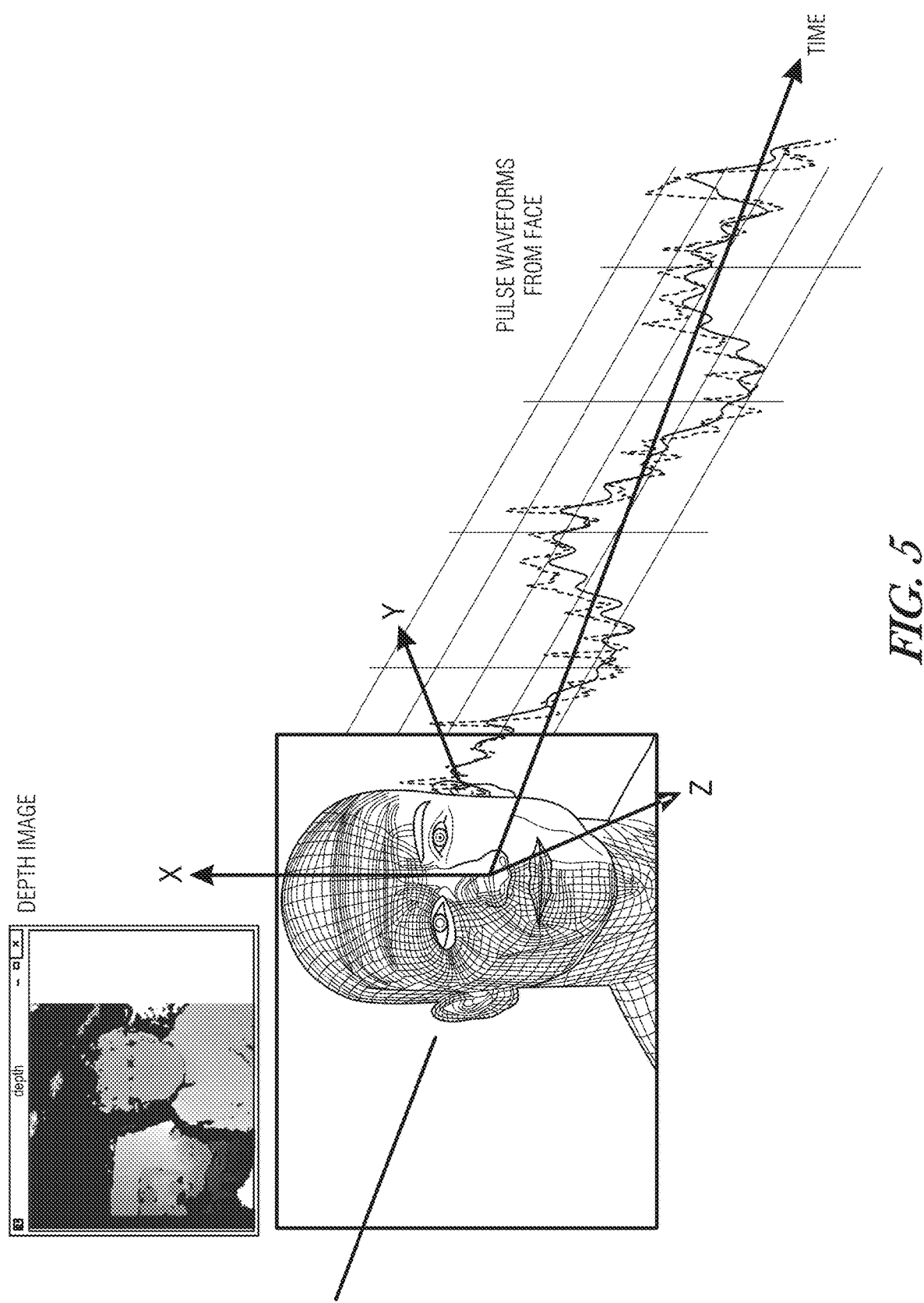
FIG. 5 is an illustration of detecting a person's heart rate, according to an embodiment.

FIG. 5 is an illustration of detecting a person's heart rate, according to an embodiment. The 3D camera may calculate a person's heart rate based on 3D voxel data (position and color) over a period of time (x, y, z, R, G, B, t), as shown in FIG. 5. Pulse waveforms are calculated based on weighted average of colors in face skin area over a three-second window. Each estimation represents the averaged value of heart beats per minute over the latest three seconds. The heart beat signal from a person's face is a periodic wave signal. However, the signal amplitude is about 1% of the 8-bit signal. To retrieve the stable signal, the system gathers at least a 90×90 pixel area of skin pixels to retrieve the pulse waveforms. Any motion greater than 1% of color value will influence the quality of the estimation. To overcome motion artifacts, the system estimates potential movement course, so that the system may then subtract the stable movement drift from the calculation. Movement may be viewed as baseline drifting or low-frequency noise. The algorithms used include a high-pass filter to extract the frequency component to reduce the influence of steady motions. However, sudden motions that have similar frequency within 1~3 hz still corrupt the signal where the system will have to discard that part of data (with higher standard deviation). Using such a mechanism, the system is able to obtain an estimated heart rate while the user is standing in front of the smart mirror.

Figure 6:
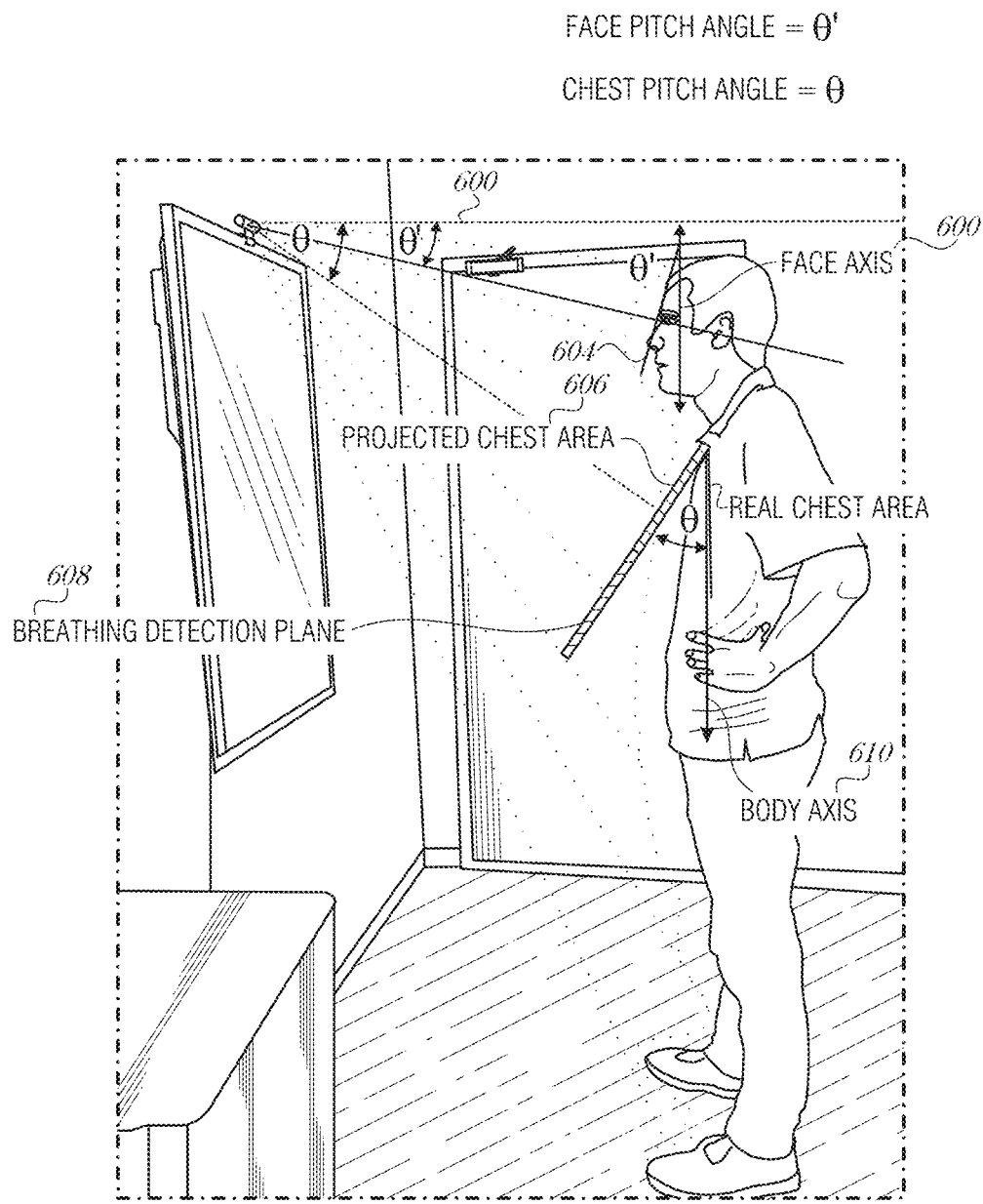
FIG. 6 is an illustration of detecting breathing patterns, according to an embodiment.

FIG. 6 is an illustration of detecting breathing patterns, according to an embodiment. The system may determine a horizontal plane 600 and a face axis 602, which is a vertical plane normal to the horizontal plane 600. A face pitch angle θ', which is an angle between the face axis 602 and the projected face area 604. A projected chest area 606 and breathing detection plane 608 may also be determined from the 3D camera, and an angle θ may be determined, where θ represents the angle between the body axis 610 and the projected chest area 606. The body axis 610 is a plane normal to the horizontal plane 600. By monitoring the breathing detection plane 608, the user's breathing patterns may be determined.

As such, breathing measurement may be viewed as detecting changes of a user's chest volume, as shown in FIG. 6. Using a 3D camera, the system is able to retrieve 3D coordinates of a person's body, including the chest area, over time. The user's breathing may then be modeled as a set of points of (x, y, z, t) in 3D with timestamps in a moving window (e.g., 30 seconds). The periodic changes in this volume space represent breathing activities. The system may simplify the calculating of this 3D volume into a few 2D projections and retrieve the same quality of breathing activities. Based on face location, user's 3D pose, and user's height, the system is able to calculate the image plane of chest area. Instead of calculating 3D volume, the system calculates the 2D expanding/shrinking projections of chest movement on image plane, because breathing expands chest area in all directions (x, y, z). By measuring the 2D projection in image plane, the smart mirror system may simplify calculations and calculate real-time activities of user's breathing.

Figure 7:
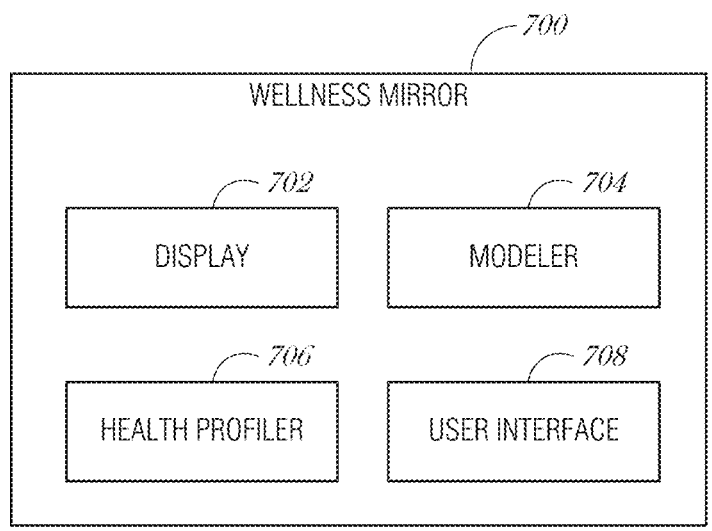
FIG. 7 is a block diagram illustrating a system for providing a wellness mirror, according to an embodiment.

FIG. 7 is a block diagram illustrating a system 700 for providing a wellness mirror, according to an embodiment. The system, the system 700 includes a display 702, a modeler 704, a health profiler 706, and a user interface 708. The display 702 may be any type of display device, such as a cathode ray tube (CRT), liquid crystal display (LCD), light emitting diode (LED), or the like. The modeler 704, health profiler 706, and user interface 708 are understood to encompass tangible entities, be that entities that are physically constructed, specifically configured (e.g., hardwired), or temporarily (e.g., transitorily) configured (e.g., programmed) to operate in a specified manner or to perform part or all of any operations described herein.

The modeler 704 may be operable to receive depth images from a depth camera that is communicatively coupled to the system, and provide a model of a subject in the depth images. In an embodiment, the modeler 704 is incorporated into the depth camera.

In an embodiment, the user interface 708 may be operable to prompt the subject to present a first view of the subject's body, and after the first view is captured by the depth camera, prompt the user to present a second view of the subject's body for capture. The modeler 704 may then compose the first view and the second view to form the model. In an embodiment, the first view is a front view of the subject and the second view is a rear view of the subject.

The health profiler 706 may be operable to analyze the model and produce a health and wellness analysis. In an embodiment, to analyze the model, the health profiler 706 is to access a height, weight, gender, and age of the subject and calculate a basal metabolic rate of the subject based on the height, weight, gender, and age. In a further embodiment, to calculate the basal metabolic rate, the health profiler is to use a Harris-Benedict equation.

In an embodiment, to analyze the model, the health profiler 706 is to access a height and a weight of the subject and calculate a body mass index of the subject. In a further embodiment, the height of the subject is measured using the model produced from the depth images. In another related embodiment, the weight of the subject is obtained from an electronic scale communicatively coupled to the system. In another related embodiment, the weight of the subject is provided by the subject and obtained from the user interface. In another related embodiment, to calculate the body mass index, the health profiler 706 is to divide the weight of the subject by the squared height of the subject and multiply the result by 703.

In an embodiment, to analyze the model, the health profiler 706 it to calculate a waist circumference and a hip circumference of the subject and calculate the body mass index of the subject based on a waist-to-hip ratio of the subject.

In an embodiment, to analyze the model, the health profiler 706 is to access a series of models of the subject produced by the modeler, calculate a periodic change in chest region over the series of models, and determine a breathing rate based on the periodic change in the chest region.

In an embodiment, to analyze the model, the health profiler 706 is to access a series of models of the subject produced by the modeler, determine a periodic change of colors in a face skin are of the subject, and estimate a heart rate based on the periodic change.

The user interface 708 may be operable to present the health and wellness analysis on the display.

In an embodiment, the user interface 708 presents the health and wellness analysis on a surface of the wellness mirror. In a related embodiment, the health and wellness analysis includes a suggested exercise. In a related embodiment, the health and wellness analysis includes a target caloric daily intake.

In an embodiment, the system 700 includes a gesture recognition module to access the depth image and identify a gesture, where the gesture indicates a user's intent to begin health and wellness analysis. Upon identifying the gesture, the gesture recognition module is to interact with the health profiler 704 and initiate the model analysis.

Figure 8:
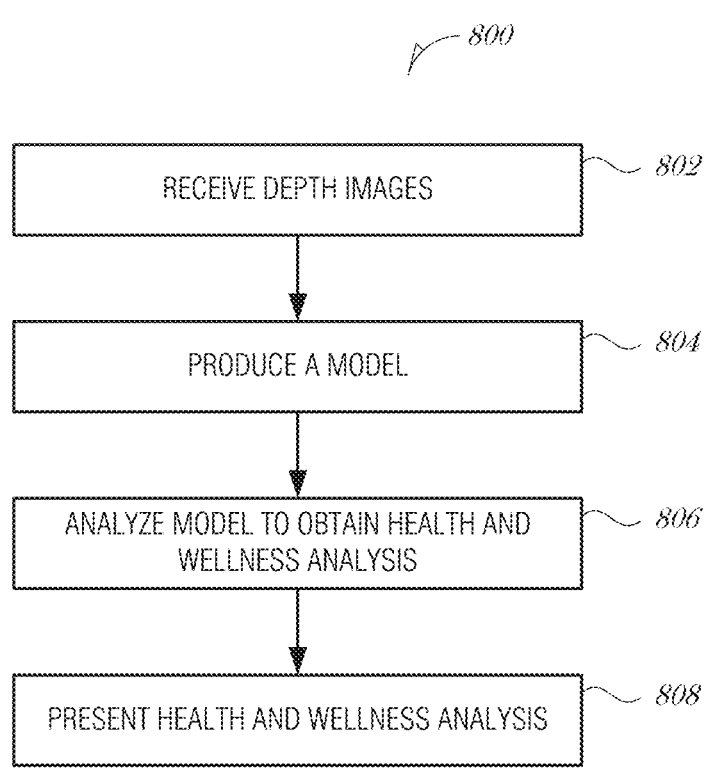
FIG. 8 is a flowchart illustrating a method of providing a wellness mirror, according to an embodiment.

FIG. 8 is a flowchart illustrating a method 800 of providing a wellness mirror, according to an embodiment. At 802, depth images from a depth camera coupled to the wellness mirror are received at the wellness mirror. In an embodiment, the method 800 includes prompting the subject to present a first view of the subject's body, and after the first view is captured by the depth camera, prompting the user to present a second view of the subject's body for capture. The method 800 may then compose the first view and the second view to form the model. In a further embodiment, the first view is a front view of the subject and the second view is a rear view of the subject.

At 804, a model of a subject in the depth images is produced. In an embodiment, producing the model is performed by the depth camera.

At 806, the model is analyzed, producing a health and wellness analysis. In an embodiment, analyzing the model includes accessing a height, weight, gender, and age of the subject, and calculating a basal metabolic rate of the subject based on the height, weight, gender, and age. In a further embodiment, calculating the basal metabolic rate includes using a Harris-Benedict equation.

In an embodiment, analyzing the model includes accessing a height and a weight of the subject, and calculating a body mass index of the subject. In a further embodiment, the height of the subject is measured using the model produced from the depth images. In a related embodiment, the weight of the subject is obtained from an electronic scale communicatively coupled to the system. In another related embodiment, the weight of the subject is provided by the subject. In an embodiment, calculating the body mass index includes dividing the weight of the subject by the squared height of the subject and multiply ing the result by 703.

In an embodiment, analyzing the model includes calculating a waist circumference and a hip circumference of the subject, and calculating the body mass index of the subject based on a waist-to-hip ratio of the subject.

In an embodiment, analyzing the model includes accessing a series of models of the subject, calculating a periodic change in chest region over the series of models, and determining a breathing rate based on the periodic change in the chest region.

In an embodiment, analyzing the model includes accessing a series of models of the subject, determining a periodic change of colors in a face skin are of the subject, and estimating a heart rate based on the periodic change.

At 808, the health and wellness analysis is presented. In an embodiment, the method 800 includes presenting the health and wellness analysis on a surface of the wellness mirror. For instance, the health and wellness analysis may be presented as a translucent layer on a mirrored surface, such that the user is able to use the mirror to see themselves, while also being able to view the user interface. In an embodiment, the health and wellness analysis includes a suggested exercise. In a related embodiment, the health and wellness analysis includes a target caloric daily intake.

In an embodiment, the method 800 includes accessing the depth image and identify a gesture, wherein the gesture indicates a user's intent to begin health and wellness analysis, and initiating the model analysis upon identifying the gesture. The gesture may be any of various arm, hand, head, or body gestures. The gesture may be configured by the user.

Embodiments may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

A processor subsystem may be used to execute the instruction on the machine-readable medium. The processor subsystem may include one or more processors, each with one or more cores. Additionally, the processor subsystem may be disposed on one or more physical devices. The processor subsystem may include one or more specialized processors, such as a graphics processing unit (GPU), a digital signal processor (DSP), a field programmable gate array (FPGA), or a fixed function processor.

Examples, as described herein, may include, or may operate on, logic or a number of components, modules, circuits, or mechanisms. Modules may be hardware, software, or firmware communicatively coupled to one or more processors in order to carry out the operations described herein. Modules may be hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

Figure 9:
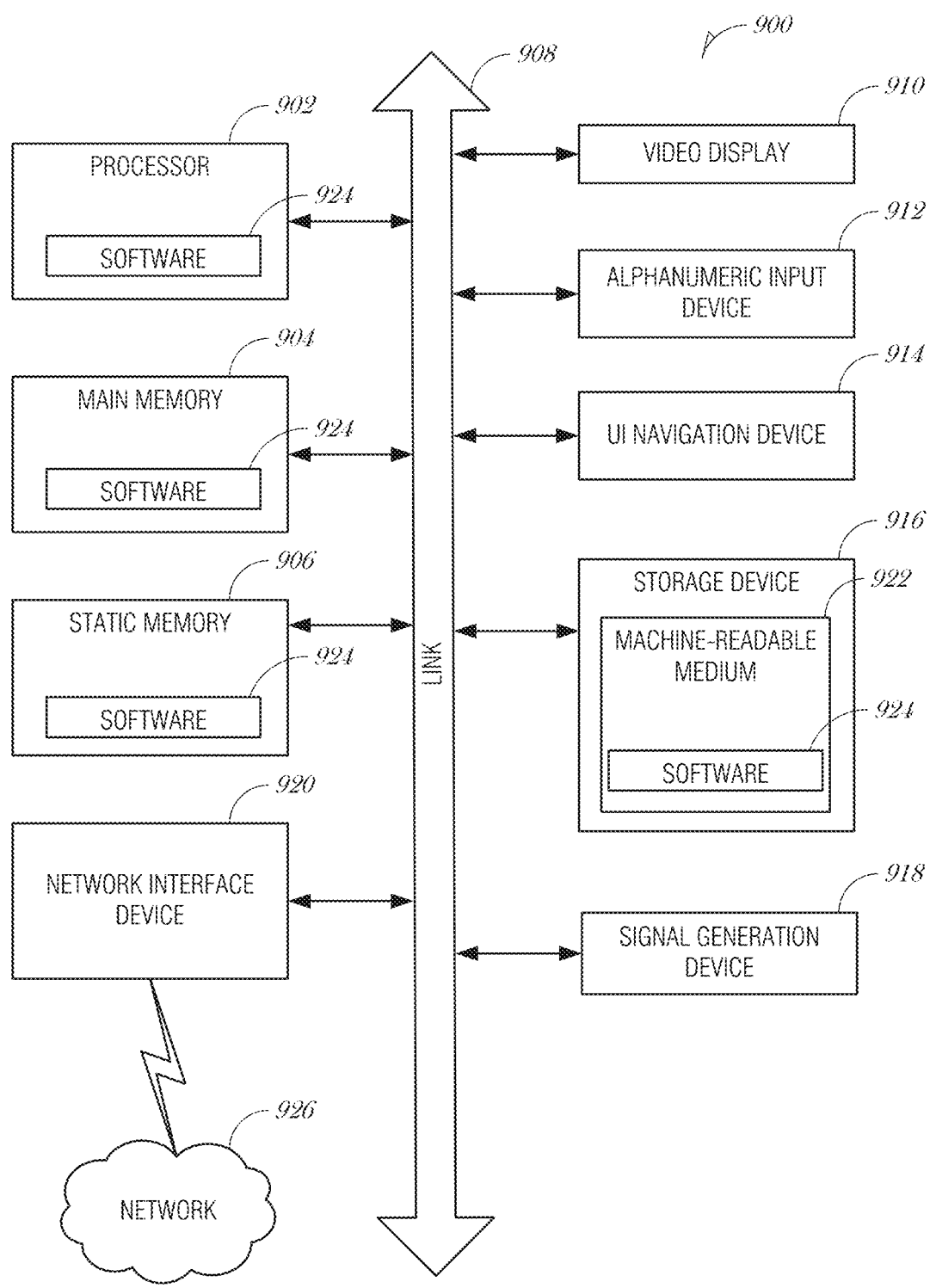
FIG. 9 is a block diagram illustrating an example machine upon which any one or more of the techniques (e.g., methodologies) discussed herein may perform, according to an example embodiment.

FIG. 9 is a block diagram illustrating a machine in the example form of a computer system 900, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a wearable device, a personal computer (PC), a tablet PC, a hybrid tablet, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 900 includes at least one processor 902 (e.g., a central processing unit (CPU), a graphics processing unit (GPU) or both, processor cores, compute nodes, etc.), a main memory 904 and a static memory 906, which communicate with each other via a link 908 (e.g., bus). The computer system 900 may further include a video display unit 910, an alphanumeric input device 912 (e.g., a keyboard), and a user interface (UI) navigation device 914 (e.g., a mouse). In one embodiment, the video display unit 910, input device 912 and UI navigation device 914 are incorporated into a touch screen display. The computer system 900 may additionally include a storage device 916 (e.g., a drive unit), a signal generation device 918 (e.g., a speaker), a network interface device 920, and one or more sensors (not shown), such as a global positioning system (GPS) sensor, compass, accelerometer, gyrometer, magnetometer, or other sensor.

The storage device 916 includes a machine-readable medium 922 on which is stored one or more sets of data structures and instructions 924 (e.g., software) embodying or utilized by any one or more of the methodologies or functions described herein. The instructions 924 may also reside, completely or at least partially, within the main memory 904, static memory 906, and/or within the processor 902 during execution thereof by the computer system 900, with the main memory 904, static memory 906, and the processor 902 also constituting machine-readable media.

While the machine-readable medium 922 is illustrated in an example embodiment to be a single medium, the term "machine-readable medium" may include a single medium or multiple media (e.g., a centralized or distributed database, and/or associated caches and servers) that store the one or more instructions 924. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 924 may further be transmitted or received over a communications network 926 using a transmission medium via the network interface device 920 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Bluetooth, Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

ADDITIONAL NOTES & EXAMPLES

Example 1 is a system for providing a wellness mirror, the system comprising: a display; a modeler to receive depth images from a depth camera that is communicatively coupled to the system, and provide a model of a subject in the depth images; a health profiler to analyze the model and produce a health and wellness analysis; and a user interface to present the health and wellness analysis on the display.

In Example 2, the subject matter of Example 1 optionally includes wherein the modeler is incorporated into the depth camera.

In Example 3, the subject matter of any one or more of Examples 1-2 optionally include wherein the user interface is to prompt the subject to present a first view of the subject's body, and after the first view is captured by the depth camera, prompt the user to present a second view of the subject's body for capture; and wherein the modeler is to compose the first view and the second view to form the model.

In Example 4, the subject matter of Example 3 optionally includes wherein the first view is a front view of the subject and the second view is a rear view of the subject.

In Example 5, the subject matter of any one or more of Examples 1-4 optionally include wherein to analyze the model, the health profiler is to: access a height, weight, gender, and age of the subject; and calculate a basal metabolic rate of the subject based on the height, weight, gender, and age.

In Example 6, the subject matter of Example 5 optionally includes wherein to calculate the basal metabolic rate, the health profiler is to use a Harris-Benedict equation.

In Example 7, the subject matter of any one or more of Examples 1-6 optionally include wherein to analyze the model, the health profiler is to: access a height and a weight of the subject; and calculate a body mass index of the subject.

In Example 8, the subject matter of Example 7 optionally includes wherein the height of the subject is measured using the model produced from the depth images.

In Example 9, the subject matter of any one or more of Examples 7-8 optionally include wherein the weight of the subject is obtained from an electronic scale communicatively coupled to the system.

In Example 10, the subject matter of any one or more of Examples 7-9 optionally include wherein the weight of the subject is provided by the subject and obtained from the user interface.

In Example 11, the subject matter of any one or more of Examples 7-10 optionally include wherein to calculate the body mass index, the health profiler is to divide the weight of the subject by the squared height of the subject and multiply the result by 703.

In Example 12, the subject matter of any one or more of Examples 1-11 optionally include wherein to analyze the model, the health profiler it to: calculate a waist circumference and a hip circumference of the subject; and calculate the body mass index of the subject based on a waist-to-hip ratio of the subject.

In Example 13, the subject matter of any one or more of Examples 1-12 optionally include wherein to analyze the model, the health profiler is to: access a series of models of the subject produced by the modeler; calculate a periodic change in chest region over the series of models; and determine a breathing rate based on the periodic change in the chest region.

In Example 14, the subject matter of any one or more of Examples 1-13 optionally include wherein to analyze the model, the health profiler is to: access a series of models of the subject produced by the modeler; determine a periodic change of colors in a face skin are of the subject; and estimate a heart rate based on the periodic change.

In Example 15, the subject matter of any one or more of Examples 1-14 optionally include wherein the user interface presents the health and wellness analysis on a surface of the wellness mirror.

In Example 16, the subject matter of any one or more of Examples 1-15 optionally include wherein the health and wellness analysis includes a suggested exercise.

In Example 17, the subject matter of any one or more of Examples 1-16 optionally include wherein the health and wellness analysis includes a target caloric daily intake.

In Example 18, the subject matter of any one or more of Examples 1-17 optionally include a gesture recognition module to access the depth image and identify a gesture, wherein the gesture indicates a user's intent to begin health and wellness analysis, and wherein upon identifying the gesture, the gesture recognition module is to interact with the health profiler and initiate the model analysis.

Example 19 is a method for providing a wellness mirror, the method comprising: receiving at the wellness mirror, depth images from a depth camera coupled to the wellness mirror, producing a model of a subject in the depth images; analyzing the model and producing a health and wellness analysis; and presenting the health and wellness analysis.

In Example 20, the subject matter of Example 19 optionally includes wherein producing the model is performed by the depth camera.

In Example 21, the subject matter of any one or more of Examples 19-20 optionally include prompting the subject to present a first view of the subject's body, and after the first view is captured by the depth camera, prompting the user to present a second view of the subject's body for capture; and composing the first view and the second view to form the model.

In Example 22, the subject matter of Example 21 optionally includes wherein the first view is a front view of the subject and the second view is a rear view of the subject.

In Example 23, the subject matter of any one or more of Examples 19-22 optionally include wherein analyzing the model comprises: accessing a height, weight, gender, and age of the subject; and calculating a basal metabolic rate of the subject based on the height, weight, gender, and age.

In Example 24, the subject matter of Example 23 optionally includes wherein calculating the basal metabolic rate includes using a Harris-Benedict equation.

In Example 25, the subject matter of any one or more of Examples 19-24 optionally include wherein analyzing the model comprises: accessing a height and a weight of the subject; and calculating a body mass index of the subject.

In Example 26, the subject matter of Example 25 optionally includes wherein the height of the subject is measured using the model produced from the depth images.

In Example 27, the subject matter of any one or more of Examples 25-26 optionally include wherein the weight of the subject is obtained from an electronic scale communicatively coupled to the system.

In Example 28, the subject matter of any one or more of Examples 25-27 optionally include wherein the weight of the subject is provided by the subject.

In Example 29, the subject matter of any one or more of Examples 25-28 optionally include wherein calculating the body mass index comprises dividing the weight of the subject by the squared height of the subject and multiplying the result by 703.

In Example 30, the subject matter of any one or more of Examples 19-29 optionally include wherein analyzing the model comprises: calculating a waist circumference and a hip circumference of the subject; and calculating the body mass index of the subject based on a waist-to-hip ratio of the subject.

In Example 31, the subject matter of any one or more of Examples 19-30 optionally include wherein analyzing the model comprises: accessing a series of models of the subject; calculating a periodic change in chest region over the series of models; and determining a breathing rate based on the periodic change in the chest region.

In Example 32, the subject matter of any one or more of Examples 19-31 optionally include wherein analyzing the model comprises: accessing a series of models of the subject; determining a periodic change of colors in a face skin are of the subject; and estimating a heart rate based on the periodic change.

In Example 33, the subject matter of any one or more of Examples 19-32 optionally include presenting the health and wellness analysis on a surface of the wellness mirror.

In Example 34, the subject matter of any one or more of Examples 19-33 optionally include wherein the health and wellness analysis includes a suggested exercise.

In Example 35, the subject matter of any one or more of Examples 19-34 optionally include wherein the health and wellness analysis includes a target caloric daily intake.

In Example 36, the subject matter of any one or more of Examples 19-35 optionally include accessing the depth image and identify a gesture, wherein the gesture indicates a user's intent to begin health and wellness analysis; and initiating the model analysis upon identifying the gesture.

Example 37 is at least one machine-readable medium including instructions, which when executed by a machine, cause the machine to perform operations of any of the methods of Examples 19-36.

Example 38 is an apparatus comprising means for performing any of the methods of Examples 19-36.

Example 39 is an apparatus for providing a wellness mirror, the apparatus comprising: means for receiving at the wellness mirror, depth images from a depth camera coupled to the wellness mirror; means for producing a model of a subject in the depth images; means for analyzing the model and producing a health and wellness analysis; and means for presenting the health and wellness analysis.

In Example 40, the subject matter of Example 39 optionally includes wherein producing the model is performed by the depth camera.

In Example 41, the subject matter of any one or more of Examples 39-40 optionally include means for prompting the subject to present a first view of the subject's body, and after the first view is captured by the depth camera, prompting the user to present a second view of the subject's body for capture; and means for composing the first view and the second view to form the model.

In Example 42, the subject matter of Example 41 optionally includes wherein the first view is a front view of the subject and the second view is a rear view of the subject.

In Example 43, the subject matter of any one or more of Examples 39-42 optionally include wherein the means for analyzing the model comprises: means for accessing a height, weight, gender, and age of the subject; and means for calculating a basal metabolic rate of the subject based on the height, weight, gender, and age.

In Example 44, the subject matter of Example 43 optionally includes wherein the means for calculating the basal metabolic rate includes using a Harris-Benedict equation.

In Example 45, the subject matter of any one or more of Examples 39-44 optionally include wherein the means for analyzing the model comprises: means for accessing a height and a weight of the subject; and means for calculating a body mass index of the subject.

In Example 46, the subject matter of Example 45 optionally includes wherein the height of the subject is measured using the model produced from the depth images.

In Example 47, the subject matter of any one or more of Examples 45-46 optionally include wherein the weight of the subject is obtained from an electronic scale communicatively coupled to the system.

In Example 48, the subject matter of any one or more of Examples 45-47 optionally include wherein the weight of the subject is provided by the subject.

In Example 49, the subject matter of any one or more of Examples 45-48 optionally include wherein the means for calculating the body mass index comprises means for dividing the weight of the subject by the squared height of the subject and multiplying the result by 703.

In Example 50, the subject matter of any one or more of Examples 39-49 optionally include wherein the means for analyzing the model comprises: means for calculating a waist circumference and a hip circumference of the subject; and means for calculating the body mass index of the subject based on a waist-to-hip ratio of the subject.

In Example 51, the subject matter of any one or more of Examples 39-50 optionally include wherein the means for analyzing the model comprises: means for accessing a series of models of the subject; means for calculating a periodic change in chest region over the series of models; and means for determining a breathing rate based on the periodic change in the chest region.

In Example 52, the subject matter of any one or more of Examples 39-51 optionally include wherein the means for analyzing the model comprises: means for accessing a series of models of the subject; means for determining a periodic change of colors in a face skin are of the subject; and means for estimating a heart rate based on the periodic change.

In Example 53, the subject matter of any one or more of Examples 39-52 optionally include means for presenting the health and wellness analysis on a surface of the wellness mirror.

In Example 54, the subject matter of any one or more of Examples 39-53 optionally include wherein the health and wellness analysis includes a suggested exercise.

In Example 55, the subject matter of any one or more of Examples 39-54 optionally include wherein the health and wellness analysis includes a target caloric daily intake.

In Example 56, the subject matter of any one or more of Examples 39-55 optionally include means for accessing the depth image and identify a gesture, wherein the gesture indicates a user's intent to begin health and wellness analysis; and means for initiating the model analysis upon identifying the gesture.

Example 57 is at least one machine-readable medium including instructions for providing a wellness mirror, which when executed by a machine, cause the machine to: receive at the wellness mirror, depth images from a depth camera coupled to the wellness mirror; produce a model of a subject in the depth images; analyze the model and producing a health and wellness analysis; and present the health and wellness analysis.

In Example 58, the subject matter of Example 57 optionally includes wherein the model is produced by the depth camera.

In Example 59, the subject matter of any one or more of Examples 57-58 optionally include instructions to: prompt the subject to present a first view of the subject's body, and after the first view is captured by the depth camera, prompt the user to present a second view of the subject's body for capture; and compose the first view and the second view to form the model.

In Example 60, the subject matter of Example 59 optionally includes wherein the first view is a front view of the subject and the second view is a rear view of the subject.

In Example 61, the subject matter of any one or more of Examples 57-60 optionally include wherein the instructions to analyze the model comprise instructions to: access a height, weight, gender, and age of the subject; and calculate a basal metabolic rate of the subject based on the height, weight, gender, and age.

In Example 62, the subject matter of Example 61 optionally includes wherein the instructions to calculate the basal metabolic rate includes instructions to use a Harris-Benedict equation.

In Example 63, the subject matter of any one or more of Examples 57-62 optionally include wherein the instructions to analyze the model comprise instructions to: access a height and a weight of the subject; and calculate a body mass index of the subject.

In Example 64, the subject matter of Example 63 optionally includes wherein the height of the subject is measured using the model produced from the depth images.

In Example 65, the subject matter of any one or more of Examples 63-64 optionally include wherein the weight of the subject is obtained from an electronic scale communicatively coupled to the system.

In Example 66, the subject matter of any one or more of Examples 63-65 optionally include wherein the weight of the subject is provided by the subject.

In Example 67, the subject matter of any one or more of Examples 63-66 optionally include wherein the instructions to calculate the body mass index comprise instructions to divide the weight of the subject by the squared height of the subject and multiply the result by 703.

In Example 68, the subject matter of any one or more of Examples 57-67 optionally include wherein the instructions to analyze the model comprise instructions to: calculate a waist circumference and a hip circumference of the subject; and calculate the body mass index of the subject based on a waist-to-hip ratio of the subject.

In Example 69, the subject matter of any one or more of Examples 57-68 optionally include wherein the instructions to analyze the model comprise instructions to: access a series of models of the subject; calculate a periodic change in chest region over the series of models; and determine a breathing rate based on the periodic change in the chest region.

In Example 70, the subject matter of any one or more of Examples 57-69 optionally include wherein the instructions to analyze the model comprise instructions to: access a series of models of the subject; determine a periodic change of colors in a face skin are of the subject; and estimate a heart rate based on the periodic change.

In Example 71, the subject matter of any one or more of Examples 57-70 optionally include instructions to present the health and wellness analysis on a surface of the wellness mirror.

In Example 72, the subject matter of any one or more of Examples 57-71 optionally include wherein the health and wellness analysis includes a suggested exercise.

In Example 73, the subject matter of any one or more of Examples 57-72 optionally include wherein the health and wellness analysis includes a target caloric daily intake.

In Example 74, the subject matter of any one or more of Examples 57-73 optionally include instructions to: access the depth image and identify a gesture, wherein the gesture indicates a user's intent to begin health and wellness analysis; and initiate the model analysis upon identifying the gesture.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A system for providing a wellness mirror, the system comprising:
a display;

a memory device; and a processor subsystem, which when configured by instructions stored in the memory device, implement:

a modeler to receive depth images from a depth camera that is communicatively coupled to the system, and provide a model of a subject in the depth images;

a health profiler to analyze the model and produce a health and wellness analysis; and a user interface to present the health and wellness analysis on the display;

wherein the user interface is to prompt the subject to present a first view of the subject's body, and after the first view is captured by the depth camera, prompt the user to present a second view of the subject's body for capture, wherein the first view is a front view of the subject and the second view is a rear view of the subject, and wherein the first and second view are aligned using a top-view image captured by a camera different than the depth camera; and wherein the modeler is to compose the model using only the first view and the second view.

2. The system of claim 1, wherein the modeler is incorporated into the depth camera.

3. The system of claim 1, wherein to analyze the model, the health profiler is to:

access a height, weight, gender, and age of the subject; and calculate a basal metabolic rate of the subject based on the height, weight, gender, and age.

4. The system of claim 3, wherein to calculate the basal metabolic rate, the health profiler is to use a Harris-Benedict equation.

5. The system of claim 1, wherein to analyze the model, the health profiler is to:

access a height and a weight of the subject; and calculate a body mass index of the subject.

6. The system of claim 5, wherein the height of the subject is measured using the model produced from the depth images.

7. The system of claim 5, wherein the weight of the subject is obtained from an electronic scale communicatively coupled to the system.

8. The system of claim 5, wherein the weight of the subject is provided by the subject and obtained from the user interface.

9. The system of claim 5, wherein to calculate the body mass index, the health profiler is to divide the weight of the subject by the squared height of the subject and multiply the result by 703.

10. The system of claim 1, wherein to analyze the model, the health profiler it to:

calculate a waist circumference and a hip circumference of the subject; and calculate the body mass index of the subject based on a waist-to-hip ratio of the subject.

11. The system of claim 1, wherein to analyze the model, the health profiler is to:

access a series of models of the subject produced by the modeler;

calculate a periodic change in chest region over the series of models; and determine a breathing rate based on the periodic change in the chest region.

12. The system of claim 1, wherein to analyze the model, the health profiler is to:

access a series of models of the subject produced by the modeler;

determine a periodic change of colors in a face skin are of the subject; and estimate a heart rate based on the periodic change.

13. The system of claim 1, wherein the user interface presents the health and wellness analysis on a surface of the wellness mirror.

14. The system of claim 1, wherein the health and wellness analysis includes a suggested exercise.

15. The system of claim 1, wherein the health and wellness analysis includes a target caloric daily intake.

16. The system of claim 1, further comprising a gesture recognition module to access the depth image and identify a gesture, wherein the gesture indicates a user's intent to begin health and wellness analysis, and wherein upon identifying the gesture, the gesture recognition module is to interact with the health profiler and initiate the model analysis.

17. A method for providing a wellness mirror, the method comprising:

prompting a subject to present a first view of the subject's body, and after the first view is captured by a depth camera coupled to the wellness mirror, and prompting the user to present a second view of the subject's body for capture by the depth camera, wherein the first view is a front view of the subject and the second view is a rear view of the subject, and wherein the first and second view are aligned using a top-view image captured by a camera different than the depth camera;

producing a model of the subject in the depth images using only the first view and the second view;

analyzing the model and producing a health and wellness analysis; and presenting the health and wellness analysis.

18. The method of claim 17, wherein producing the model is performed by the depth camera.

19. At least one non-transitory machine-readable medium including instructions for providing a wellness mirror, which when executed by a machine, cause the machine to:

prompt a subject to present a first view of the subject's body, and after the first view is captured by a depth camera coupled to the wellness mirror, and prompt the user to present a second view of the subject's body for capture by the depth camera, wherein the first view is a front view of the subject and the second view is a rear view of the subject, and wherein the first and second view are aligned using a top-view image captured by a camera different than the depth camera;

produce a model of the subject in the depth images using only the first view and the second view;

analyze the model and producing a health and wellness analysis; and present the health and wellness analysis.

20. The non-transitory machine-readable medium of claim 19, wherein the instructions to analyze the model comprise instructions to:

access a height and a weight of the subject; and calculate a body mass index of the subject.

21. The non-transitory machine-readable medium of claim 20, wherein the height of the subject is measured using the model produced from the depth images.

* * * * *